(12) United States Patent
Vincent

(10) Patent No.: US 7,354,953 B2
(45) Date of Patent: Apr. 8, 2008

(54) TIME-RELEASE COMPOSITIONS FOR DELIVERY OF [CR₃O(CARBOXYLATE)₆(H₂O)₃]⁺

(75) Inventor: John B. Vincent, Tuscaloosa, AL (US)

(73) Assignee: University of Alabama, Tuscaloosa, AL (US)

( * ) Notice: Subject to any disclaimer, the term of this patent is extended or adjusted under 35 U.S.C. 154(b) by 0 days.

(21) Appl. No.: 11/392,503

(22) Filed: Mar. 30, 2006

(65) Prior Publication Data

US 2007/0231383 A1    Oct. 4, 2007

(51) Int. Cl.
*A61K 31/28* (2006.01)
*A61K 33/24* (2006.01)
*A61P 3/10* (2006.01)

(52) U.S. Cl. ............... 514/505; 514/184; 514/185; 514/866; 424/655

(58) Field of Classification Search ......... 514/184, 514/185, 505, 866; 424/655
See application file for complete search history.

(56) References Cited

U.S. PATENT DOCUMENTS

| | | | |
|---|---|---|---|
| 4,753,911 A | 6/1988 | Goe et al. | 502/159 |
| 6,149,948 A | 11/2000 | Vincent | |
| 6,197,816 B1 | 3/2001 | Vincent et al. | |
| 6,444,231 B2 | 9/2002 | Vincent et al. | |
| 6,764,524 B1 | 7/2004 | Körte | 8/522 |
| 6,881,752 B2 | 4/2005 | Vincent et al. | |
| 2006/0003981 A1 | 1/2006 | Fine et al. | 514/184 |

OTHER PUBLICATIONS

Gavrilenko, K.S. et al., "Magnetic characteristics of trinuclear complexes [M3O(CH3COO)6(pz)3]+ (M=Fe, Cr; pz=pyrazine)," Theoretical and Experimental Chemistry, vol. 40(4), pp. 214-219 (2004).*
HCAPLUS Abstract 1999:341777 (1999).*

* cited by examiner

*Primary Examiner*—John Pak
(74) *Attorney, Agent, or Firm*—Oblon, Spivak, McClelland, Maier & Neustadt, P.C.

(57) ABSTRACT

A time release composition is provided containing:
a chromium complex having formula 3

$$[Cr_3O(carboxylate)_6(ligand)_3]^+ \qquad (3)$$

wherein carboxylate is a C2-C5 alkyl carboxylate and wherein 'ligand' is a ligand that (i) renders the chromium complex insoluble or only slightly soluble in water and (ii) is acid labile, being readily displaced under acidic conditions below pH=4 and replaced by water to make the resulting water soluble complex 2

$$[Cr_3O(carboxylate)_6(H_2O)_3]^+, \qquad (2)$$

and the use of the time release composition for the time release delivery of complex 2.

7 Claims, No Drawings

TIME-RELEASE COMPOSITIONS FOR DELIVERY OF [CR$_3$O(CARBOXYLATE)$_6$(H$_2$O)$_3$]$^+$

BACKGROUND OF THE INVENTION

1. Field of Invention

The present invention relates to methods and compositions for the time released delivery of triaqua-mu3-oxo-hexakis-mu-alkylcarboxylatotrichromium (1+), [Cr$_3$O(carboxylate)$_6$ (H$_2$O)$_3$]$^+$.

2. Discussion of the Background

In the late 1950s and 1960s, rats fed a chromium-deficient diet were found to possess a decreased ability to repress blood glucose concentrations, while chromic ions were shown to increase the efficiency of insulin action in rat epididymal tissue [1-5]. Since these observations, a search has been underway to identify the biologically active form of chromium, that is, the biomolecule which naturally binds chromium (III) and possesses an intrinsic function associated with insulin action in mammals [6-8]. The average American diet contains only about 30 μg Cr per day [9, 10], which has resulted in the development of chromium-containing dietary supplements. Such materials also have potential as insulin-potentiating therapeutics which could possibly see use in the treatment of diabetes and related conditions [11]. Determining the structure, function, and mode of action of the biologically active form of chromium could greatly aid in the rational design of such potential therapeutics.

The first chromium-containing species proposed to be biologically active was glucose tolerance factor(GTF)[1,12]. GTF was first isolated from acid-hydrolyzed porcine kidney powder, although a similar, if not identical, material was subsequently isolated from yeast[1,13]. Currently the term GTF is usually understood to refer to only the material isolated from yeast. GTF is absorbed better than simple chromic salts and potentiates insulin action in rat epididymal tissue or isolated rat adipocytes [14]. However, kinetics studies indicate that GTF does not intrinsically possess biological activity [15]; additionally, the material is apparently a byproduct of the acid hydrolysis step used in its purification [16].

GTF was proposed to be composed of chromic ion, nicotinic acid, and the amino acids glycine, glutamic acid and cysteine [13]. While these results have not been reproducible in some laboratories [17-21], this report stimulated an intense interest in the synthesis of chromic-nicotinate complexes [22-25], some of which have been patented as nutritional supplements. The proposed identification of nicotinic acid (2-carboxypyridine) also stimulated investigations of complexes of chromium(III) with the related pyridine carboxylic acids picolinic acid (2-carboxypyridine) and isonicotinic acid (4-carboxypyridine) [26-28]. As a result chromium(III) tris(picolinate), Cr(pic)$_3$, has become a very popular nutritional supplement and is being tested as a therapeutic for the treatment of symptoms of adult-onset diabetes. It is available over-the-counter in the form of pills, chewing gums, sport drinks, and nutrition bars. Cr(pic)$_3$ is also a well absorbed form of chromium and has been proposed to be the biologically active form of chromium [29]. This is, however, extremely doubtful given the chemistry required to synthesize this material.

In the last decade, a number of investigators have examined the effects of administering Cr(pic)$_3$ (and in some cases other forms of chromium(III)) to rats on regular diets [30-33]. After an initial preliminary report which suggested beneficial effects on blood variables [30], detailed examinations of the effect of Cr(pic)$_3$ administration in amounts up to 1500 μg/kg diet for up to 24 weeks have found no acute toxic effects [31-33]. However, the compound and other chromium sources examined (most notably "Cr nicotinate" and chromium chloride) also had no effect on body mass, percentage lean or fat content, tissue size (heart, testes, liver, kidney, muscle, epididymal fat, spleen, and kidney), or blood variables (fasting glucose, insulin, cholesterol, etc.). No differences in the gross histology of the liver or kidney (organs where chromium(III) preferentially accumulated) were found, although chromium did accumulate in these organs [33]. Another study compared the effects of a Cr-deficient diet with diets supplemented with ten different sources of chromium, including allowing rats to live in stainless steel cages. The Cr sources had no effect on body mass; all but one source decreased epididymal fat. Testes and liver masses tended to be lowered, whereas kidney, heart, and spleen masses were not significantly altered. Supplemental Cr had no effect on serum triglycerides or cholesterol, and only one source resulted in lower serum glucose [34]. While these studies did not manifest any acute toxicity, the lack of beneficial effects of Cr(pic)$_3$ supplementation on growth, fat content or glucose, insulin, or cholesterol concentrations raises questions about its therapeutic potential. Recently the safety of intaking Cr(pic)$_3$ has been questioned, especially in regards to its potential to cause clastogenic damage [35,36]. At physiologically-relevant concentrations of chromium (120 nM) and biological reductants such as ascorbic acid and thiols (5 mM), Cr(pic)$_3$ has been shown to catalytically produce hydroxyl radicals which cleave DNA[35]. This ability stems from the combination of chromium and picolinate; the picolinate ligands prime the redox potential of the chromic center such that it is susceptible to reduction. The reduced chromium species interacts with dioxygen to produce reduced oxygen species including hydroxyl radical. These studies are in agreement with earlier studies which showed that mutagenic forms of chromium (III) required chelating ligands containing pyridine-type nitrogens coordinated to the metal [37].

Recently the naturally-occurring oligopeptide low-molecular-weight chromium-binding substance, LMWCr, has been proposed as a candidate for the biologically active form of chromium [6,7,38,39]. Kinetics studies of insulin action on rat adipocytes suggest that LMWCr has an intrinsic function in insulin-sensitive cells [15,40]. The oligopeptide appears to be part of an insulin signal amplification mechanism [6,7]. The oligopeptide containing four chromic ions binds to insulin-activated insulin receptor, stimulating its tyrosine kinase activity up to eight-fold with a dissociation constant of approximately 100 pM [38]. Spectroscopic studies have shown that LMWCr possesses a multinuclear chromic assembly where the chromic centers are bridged by anionic ligands (presumably oxide and/or hydroxide). The assembly is supported by carboxylate groups from aspartate and glutamate residues from the oligopeptide [41]. This discovery has spurred an interest in the synthesis and characterization of multinuclear oxo(hydroxo)-bridged chromium(III) carboxylate assembles [42-45]. In 1997, such an assembly, [[Cr$_3$O(O$_2$CCH$_2$CH$_3$)$_6$(H$_2$O)$_3$]$^+$, 1, was found to mimic the ability of LMWCr to stimulate insulin receptor kinase activity [39]. Both LMWCr and the biomimetic 1 have been proposed as potential nutritional supplements and therapeutics. Both LMWCr and 1 have been shown not to lead to DNA cleavage [46]. The synthetic complex has several potential benefits over the natural material: it is inexpensive to synthesize and can be readily prepared in bulk. LMWCr is susceptible to hydrolysis, especially in the presence of acid, whereas the synthetic material can be recrystallized from dilute mineral acid [47] and could potentially survive oral ingestion. After the insulin signaling event, LMWCr may be excreted in the urine [48,49], and it is possible the body might target the material for excretion rather than absorption.

The biologically-active, naturally-occurring oligopeptide low-molecular-weight chromium-binding substance (LM-WCr) has been found to activate the insulin-dependent tyrosine protein kinase activity of insulin receptor (IR) approximately eightfold with a dissociation constant of circa 250 pM. [38] This activity is directly proportional to the Cr content of the oligopeptide (being maximal at four chromic ions per oligopeptide), while substitution of chromium with metal ions commonly associated with biological systems results in inactivating the oligopeptide. Similarly, LMWCr has been reported to activate a membrane-associated phosphotyrosine phosphatase; this activation also requires four chromic ions per oligopeptide to be maximal, while chromic ions could not functionally be replaced with other transition metal ions. [50] A role for LMWCr in amplification of insulin-signaling has been postulated. [38,41]. Chromium is mobilized from the blood and taken up by insulin-dependent cells in response to insulin. [51] LMWCr is maintained in its apo form [52] but possesses a large chromic ion binding constants(s) as it is capable of removing chromium from Cr-transferring. [52,53] The holo LMWCr is then capable of stimulating IR kinase activity, amplifying the signal of insulin into the insulin-dependent cells. An association between chromium and insulin-dependent glucose and lipid metabolism has been reported for nearly four decades; [54] however, only recently since procedures for isolation of quantities of LMWCr suitable for kinetic and spectroscopic studies have been developed. [41] has progress been made in understanding the association on a molecular level.

An association between the essential nutrient chromium and adult-onset diabetes has also been postulated. [55] Anderson and coworkers found improved glycemic control for 180 adult-onset diabetic patients following chromium supplementation, [56] while Ravina and Slezack using 138 adult-onset diabetic patients found reduced insulin requirements. [57] Unfortunately, the form of chromium used as a dietary supplement in these studies, chromium(III) picolinate, has been found to cause chromosome damage. [58] This suggests that a new form of chromium for use as a dietary supplement and as part of a potential treatment for adult-onset diabetes is required.

LMWCr would appear to be a possibility. It has a high $LD_{50}$[53] and is biologically active, opposed to chromium picolinate and glucose tolerance factor (a material isolated from acid-hydrolyzed Brewer's yeast extracts) which serve only as sources of readily absorbable chromium. [59] However, LMWCr is susceptible to hydrolysis under acidic conditions[16] and consequently could not be taken orally without degradation.

Recent studies have shown that biomimetic 1 is absorbed with 40-60% efficiency over a wide range of dosage, a significant improvement over the 0.5-2% absorption of other chromium supplements such as chromium chloride, chromium nicotinate, and chromium picolinate. [60] However, 1 is absorbed and enters tissues very quickly such that methods to maintain levels of 1 would be of value. Accordingly, there remains a need for improved dietary supplements.

REFERENCES

1. Schwarz K, Mertz W (1959) Arch Biochem Biophys 85: 292.
2. Mertz W, Schwarz K (1959) J Physiol 196: 614.
3. Mertz W, Roginski E E, Schwarz K (1961) J Biol Chem 236: 318.
4. Mertz W, Roginski E E (1963) J Biol Chem 238: 868.
5. Mertz W, Roginski E E, Schroeder H A (1965) J Nutr 86: 107.
6. Davis C M, Vincent J B (1997) J Biol Inorg Chem 2: 675.
7. Vincent J B (1999) J Am Coll Nutr 18: 6.
8. Lukaski H C (1999) Ann. Rev. Nutr. 19: 279.
9. Anderson R A, Koziovsky A S (1985) Am J Clin Nutr 41: 768.
10. Anderson R A (1994) In: Mertz W, Abernathy C O, Olin S S (eds) Risk Assessment of Essential Elements. ISLI Press, Washington, pp. 187-196.
11. Anderson R A (1998) J Am Coll Nutr 17: 548.
12. Schwarz K, Mertz W (1957) Arch Biochem Biophys 72: 515.
13. Toepfer E W, Mertz W, Polansky M M, Roginski W W, Wolf W R (1977) J Agric Food Chem 25: 162.
14. Anderson R A, Brantner J H, Polansky M M (1998) J Agric Food Chem 26: 1219.
15. Vincent J B (1994) J Nutr 124: 117.
16. Sumrall K K, Vincent J B (1997) Polyhedron 16: 4171.
17. Gonzalez-Vergara E, Hegenauer J, Saltman P (1982) Fed Proc 41: 286.
18. Haylock S J, Buckley P D, Blackwell L F (1983) J Inorg Biochem 18: 195.
19. Mirsky N, Weiss A, Dori Z (1980) J Inorg Biochem 13: 11.
20. Kumpulainen J, Koivistoinen P, Lahtinen S (1978) Bioinorg Chem 8: 419.
21. Votava H J, Hahn C J, Evans G W (1973) Biochem Biophys Res Commun 55: 312.
22. Gonzalez-Vergara E, Hegenauer J, Saltman P, Sabat M, Ibers J A (1982) Inorg Chim Acta 66: 115.
23. Gerdom L E, Goff E M (1982) Inorg Chem 21: 3847.
24. Chang J C, Gerdom L E, Baenziger N C, Goff H M (1983) Inorg Chem 22: 1739.
25. Cooper J A, Anderson B F, Buckley P D, Blackwell L F (1984) Inorg Chim Acta 91: 1.
26. Bradshaw J E, Grossie D A, Mullica D F, Pennington D E (1988) Inorg Chim Acta 141: 41.
27. Steams D M, Armstrong W H (1992) Inorg Chem 31: 5178.
28. Evans G W, Pouchnik D J (1993) J Inorg Biochem 49: 177.
29. Evans G W, Bowman T D (1992) J Inorg Biochem 46: 243.
30. Evans G W, Meyer L (1992) Age 15: 134.
31. Hasten D L, Hegsted N L Keenan M J, Morris G S (1997) Nutr Res 17: 283.
32. Hasten D L, Hegsted M. Keenan M J, Morris G S (1997) Nutr Res 17: 1175.
33. Anderson R A, Bryden N A, Polansky M M (1997) J Am Coll Nutr 6:273.
34. Anderson R A, Bryden N A, Polansky M M, Gautschi K (1996) J Trace Elem Exp Med 9:11.
35. Speetjens J K, Collins R A, Vincent J B, Woski S A (1999) Chem Res Toxicol, 12:483.
36. Stearns D M, Belbruno J J, Wetterhahn K E (1995) FASEB J 9: 1650.
37. Sugden K D, Geer R D, Rogers S J (1992) Biochemistry 31: 11626.

38. Davis C M, Vincent J B (1997) Biochemistry 36: 4382.
39. Davis C M, Vincent J B (1997) Inorg Chem 36: 5316.
40. Yamamoto A, Wada O, Suzuki H (1988) J Nutr 118: 39.
41. Davis C M, Vincent J B (1997) Arch Biochem Biophys 339: 335.
42. Harton A, Terrell K, Huffman J C, MacDonald C, Beatty A, Li S, O'Connor C, Vincent J B (1997) Inorg Chem 36: 4875.
43. Donald S, Terrell K, Robinson K, Vincent J B (1995) Polyhedron 14: 971.
44. Ellis T, Glass M, Harton A, Folting K, Huffman J C, Vincent J B (1995) Inorg Chem 33:5522.
45. Nagi M, Harton A, Donald S, Lee Y-S, Sabat M, O'Connor C J, Vincent J B (1995) Inorg Chem 34: 3813.
46. Speetjens J K, Parand A, Crowder Vincent J B, Woski S A (1999) Polyhedron 18:2617.
47. Johnson M K, Powell D B, Cannon R D (1981) Spectrochim Acta 37A: 995.
48. Anderson R A, Polansky M M, Bryden N A, Roginski E E, Patterson K Y, Reamer D C (1982) Diabetes 31: 212.
49. Wada O, Wu G Y, Yamamoto A, Manabe S, Ono T (1983) Environ Res 32: 228.
50. Davis, C. M.; Sumrall, K. H.; Vincent, J. B. (1996) Biochemistry 35: 12963.
51. Morris, B. W.; Blumsohn, A.; McNeil, S.; Gray, T. A. Am. J. Clin. Nutr. 1992, 55, 989; Morris, B. W.; Gray, T. A.; MacNeil, S. Clin. Sci. 1993, 84, 477; Morris, B. W.; MacNeil, S.; Stanley, K.; Gray, T. A.; Fraser, R. J. (1993) Endocrin. 139: 339.
52. Yamamoto, A.; Wada, O.; Ono, T. (1987) Eur. J. Biochem. 165: 627.
53. Yamamoto, A.; Wada, O.; Ono, T. (1984) J. Inorg. Biochem. 22: 91.
54. Mertz, W.; Roginski, E. E.; Schwartz, K. (1961) J. Biol. Chem. 236: 318; Mertz, W.; Roginski, E. E. (1963) J. Biol. Chem. 238: 868; Mertz, W. (1993) J. Nutr. 123: 626; Vincent, J. B. (1994) In Encyclopedia of Inorganic Chemistry; King, B., Ed.; John Wiley: New York, ; Vol. 2, pp 661-665.
55. Anderson, R. A. (1992) Biol. Trace Elem. Res. 32: 19.
56. Anderson, R. A.; Cheng, N.; Bryden, N.; Polansky, M.; Cheng, N.; Chi, J.; Feng, (1996) J. Diabetes 45: Suppl. 2, 124A.
57. Ravina, A.; Slezack, L. (1993) Harefuah 125: 142.
58. Stearns, D. M.; Wise, J. P., Jr.; Patierno, S. R.; Wetterhahn, K. E. (1995) FASEB J. 9: 1643.
59. McCarty, M. F. J. Opt. Nutr. 1993, 2, 36; Vincent, J. B. (1994) J. Nutr. 124: 117.
60. Clodfelder, B. J.; Chang, C.; Vincent, J. B. (2004) Biol. Trace Elem. Res. 98: 159.
61. Vemura, S.; Spemcer, A.; Wilkinson, G. (1973) J. Chem. Soc., Dalton Trans. 2565.

SUMMARY OF THE INVENTION

Accordingly, one object of the present invention is to provide a time release composition for delivery of chromium complex 2

$$[Cr_3O(carboxylate)_6(H_2O)_3]^+ \quad (2).$$

A further object of the present invention is to provide a method for time release delivery of chromium complex 2 to a subject in need thereof.

These and further objects of the present invention have been satisfied, either individually or in combinations, by the discovery of a time release composition, comprising:

a chromium complex having formula 3

$$[Cr_3O(carboxylate)_6(ligand)_3]^+ \quad (3)$$

wherein carboxylate is a C2-C5 alkyl carboxylate and wherein 'ligand' is a ligand that (i) renders the chromium complex insoluble or only slightly soluble in water and (II) is acid labile, being readily displaced under acidic conditions below pH=4 and replaced by water to make the resulting water soluble complex 2

$$[Cr_3O(carboxylate)_6(H_2O)_3]^+ \quad (2); and$$

its use in the time release delivery of chromium complex 2 by administration to a subject in need thereof.

DETAILED DESCRIPTION OF THE INVENTION

The present invention relates to a time release composition for time release delivery of $[Cr_3O(carboxylate)_6(H_2O)_3]^+$, 2. The present composition comprises a derivative of 2 $[Cr_3O(carboxylate)_6(H_2O)_3]^+$ in which the three terminal water ligands have been replaced by a ligand that renders the resulting compound insoluble or of limited solubility in water, while being displaced under acidic conditions, such as in the stomach, and replaced by water.

Complex 1, noted above, has been shown in healthy and model type 2 diabetic rats to increase insulin sensitivity and improve blood plasma cholesterol and triglycerides levels and to reduce glycated hemoglobin in the diabetes models. Complex 1 has also been shown to reduce the onset of colorectal cancer in rat. Complex 1 is absorbed very rapidly and very efficiently compared to other chromium-containing nutritional supplements. It also dissolves in water very rapidly. Thus, unfortunately, the complex does not stay in the body very long. It gets absorbed, has a chance to exert an effect on the body, breaks down and clears the body rapidly. In order to get the maximum benefit from taking Complex 1, or similar complexes having formula 2, a person would have to take small doses of the complex multiple times per day.

The present invention composition, however, provides complexes of formula $[Cr_3O(carboxylate)_6(ligand)_3]^+$, 3, wherein carboxylate is a C2-C5 alkyl carboxylate and wherein 'ligand' is a ligand that renders the complex insoluble or only slightly soluble in water and is acid labile, being readily displaced under acidic conditions below pH=4 and replaced by water to make the resulting complex 2 which is water soluble. Additionally the ligand must be non-toxic, at least in the levels that would be generated within the body during displacement. More preferably, the ligand would also be excreted or metabolized to avoid buildup of any toxic concentrations of the ligand after displacement. Preferably the carboxylate group is acetic, propionic, n-butyric or n-pentanoic, most preferably propionic. Preferably the ligand is a nitrogen containing heterocycle, such as pyridine, pyrrolidone, piperazine, and imidazole, and is most preferably pyridine.

Using the complex 3 of the present invention, the subject can take the present composition 1-3 times per day, preferably 1-2 times per day, most preferably once a day, alone or in conjunction with a complex such as 1 or 2, with the present invention complex 3 being converted over time in the stomach or small intestine into complex 2, thus allowing the active and soluble complex 2 to enter the body over a period of time rather than all at once. When taken in conjunction with a dose of complex 2 itself, complex 2 would be essentially immediately absorbed then additional complex 2 created and absorbed over time. This would eliminate the need for multiple (4 or more) dosing during the day.

Chromium complex 3 can be used to supplement the diet of animals with chromium. The complex is preferably administered to the patient in a manner such that the complex comes into contact with conditions that are sufficiently acidic to cause the displacement of the ligand by water, most preferably by oral administration as, for example, an aqueous solution, dispersion or suspension. These solutions, dispersions and suspensions may contain all of the customary additives well known to those of skill in the art, e.g., buffering agents, salts (e.g., NaCl), sugars (e.g., glucose and lactose), etc. Alternatively, the complex can be formulated into a solid dosage form, such as a tablet, pill, capsule or caplet, suitable for oral ingestion. The daily dosage of complex 3 may vary over a wide range, such as 5 to 10,000 micrograms of Cr per day, including all specific values and subranges therebetween. Dosage is measured based on the amount of Cr delivered on a daily basis.

Complex 3 may be used as a chromium dietary supplement to maintain good health and nutrition. Complex 3 may also be used to treat medical conditions which are associated with chromium deficiency or conditions which are ameliorated by increasing bodily levels of chromium.

Complex 3 converts into complex 2 which activates insulin receptor protein tyrosine kinase activity. Accordingly, administering the complex may be used as a method of treating adult-onset diabetes. In addition, it is known that cardiovascular diseases are associated with chromium deficiencies. Accordingly, cardiovascular diseases may be effectively treated by administering complex 3 to patients.

Complex 3 may also be used as a component of an animal nutrient composition. Such a composition contains chromium complex 3 and at least one pharmacologically acceptable excipient. Suitable excipients are well-known and include diluents, disintegrators, binders and lubricants (glidants). Specific examples include, for example, celluloses, gelatins, starches, polysorbate 80, oils (e.g., peanut oil, fish liver oil). Preferably, the nutritive composition is made to U.S. Pharmacopiea quality, purity and potency standards. The nutrient composition is preferably in the form of a solid. For a description of solid compositions, see Pharmaceuticals, Kirk-Othmer Encyclopedia of Chemical Technology, Fourth Edition, Volume 18, pp. 480-510, incorporated herein by reference.

The nutritive composition may also contain at least one additional animal nutrient. As used herein the term "animal nutrient" refers to compounds and substances which are recognized to maintain and regulate bodily functions. Specific examples of additional animal nutrients include vitamins (e.g., vitamin A, beta carotene, vitamin B.sub.1, vitamin B.sub.2, vitamin B.sub.6, vitamin B.sub.12, vitamin C, vitamin D, vitamin E, vitamin K), minerals (e.g., calcium, iron, copper, selenium, zinc, magnesium), enzyme cofactors, iodine, phosphorous, folate, biotin, and niacin.

Complex 3 may also be used as a component of a pharmaceutical composition. Such a composition contains chromium complex 3 and at least one additional pharmaceutical agent. As used herein the term "pharmaceutical agent" refers to compounds and substances which are recognized to as treatment and or therapies for a disease state, e.g., drugs. Specific examples of the pharmaceutical agent include insulin and other anti-diabetes medications. For a discussion of insulin and other antidiabetes medicines, see Insulin and Other Antidiabetic Agents, Kirk-Othmer Encyclopedia of Chemical Technology, Fourth Edition, Volume 14, pp. 662-676, incorporated herein by reference. The pharmaceutical composition may also contain any of the well-recognized excipients discussed above. The pharmaceutical composition is preferably in a solid dosage form as discussed above.

As used herein, the terms "animal" and "patient" include humans and non-human animals. A particularly preferred group of non-human animals are mammals (such as farm animals, cats and dogs).

Since 3 is a cation, the complex will, of course, be in the form of a salt with an anion. The anion should be non-toxic when used in the methods according to the present invention, i.e., the anion is pharmcologically acceptable. The anion is preferably the salt of a pharmcologically acceptable inorganic or organic acid. Specific examples of suitable anions include nitrate, sulfate, chloride, bromide, iodide, and phosphate.

Having generally described this invention, a further understanding can be obtained by reference to certain specific examples which are provided herein for purposes of illustration only and are not intended to be limiting unless otherwise specified.

EXAMPLES

The acetate derivative of complex 3 (wherein carboxylate=acetate) was prepared having pyridine ligands as the terminal ligands. [61] This acetate derivative (0.25 grams) was placed into 10 milliliters of 1.2 molar hydrochloric acid to simulate the pH conditions at the surface of the stomach. A second sample of the same acetate derivative (0.25 grams) was placed into 10 milliliters of 0.12 molar hydrochloric acid to simulate gastric fluid. The samples were occasionally agitated. After just under five hours, the samples were centrifuged to separate solid from liquid and an ultraviolet/visible spectrum was collected to determine the presence of complex 2 wherein carboxylate=acetate. It was found that the hydrolysis of acetate complex 3 into acetate complex 2 did occur.

This application is related to U.S. Pat. Nos. 5,872,102; 6,149,948; 6,197,816 and 6,444,231, the entire contents of each of which are hereby incorporated by reference.

The invention claimed is:

1. A method for time release delivery of chromium complex 2

$$[Cr_3O(carboxylate)_6(H_2O)_3]^+ \qquad (2)$$

comprising:
  administering to a subject in need thereof a time release composition, comprising:
  a chromium complex having formula 3

$$[Cr_3O(carboxylate)_6(ligand)_3]^+ \qquad (3)$$

wherein carboxylate is a C2-C5 alkyl carboxylate and wherein the ligand is a ligand that (i) renders the chromium complex insoluble or only slightly soluble in water and (ii) is acid labile, being readily displaced under acidic conditions below pH=4 and replaced by water to make the resulting water soluble complex 2

$$[Cr_3O(carboxylate)_6(H_2O)_3]^+ \qquad (2).$$

2. The method of claim 1 wherein the time release composition further comprises a carrier.

3. The method of claim 1 wherein the time release composition further comprises a single dose of chromium complex 2.

4. The method of claim 1, wherein carboxylate is acetate or propionate.

5. The method of claim 1, wherein ligand is a nitrogen containing heterocycle.

6. The method of claim 5, wherein ligand is a member selected from pyridine, pyrrolidone, piperazine and imidazole.

7. The method of claim 4, wherein ligand is pyridine.

* * * * *